United States Patent
Nakamura (10) Patent No.: US 7,547,137 B2
(45) Date of Patent: Jun. 16, 2009

(54) FREEZING POINT TEMPERATURE MEASURING METHOD AND TEMPERATURE CALIBRATING METHOD IN DIFFERENTIAL SCANNING CALORIMETRY

(75) Inventor: Toshihiko Nakamura, Chiba (JP)

(73) Assignee: SII Nano Technology Inc., Chiba (JP)

( * ) Notice: Subject to any disclaimer, the term of this patent is extended or adjusted under 35 U.S.C. 154(b) by 78 days.

(21) Appl. No.: 11/706,823

(22) Filed: Feb. 13, 2007

(65) Prior Publication Data

US 2007/0242722 A1    Oct. 18, 2007

(30) Foreign Application Priority Data

Feb. 13, 2006    (JP)    ............... 2006-035265

(51) Int. Cl.
G01N 25/04 (2006.01)
G01K 15/00 (2006.01)
G01K 19/00 (2006.01)
G01K 3/00 (2006.01)

(52) U.S. Cl. ............... 374/27; 374/102; 374/10; 374/1; 374/43

(58) Field of Classification Search ............... 374/1, 374/27, 102, 104, 25, 10, 43
See application file for complete search history.

(56) References Cited

U.S. PATENT DOCUMENTS 4,601,587 A *   7/1986  Mathiprakasam   ............ 374/25
5,711,604 A *   1/1998  Nakamura   ................... 374/44
2008/0049810 A1*  2/2008  Schick   ........................ 374/31

FOREIGN PATENT DOCUMENTS

JP    2000-028559    1/2000

OTHER PUBLICATIONS

Japanese Industrial Standards JIS K 7121: 1987, "transition temperature measuring method of plastic" (paragraphs 4-5, Fig. 2, example of method of acquiring crystallizing temperature).
ISO 11357-1: 1997, "Plastics-Differential scanning calorimetry (DSC)-Part 1: General principles," p. 33. 10 characteristic temperatures, p. 5, 8. 2 Temperature calibration.
Japanese Industrial Standards JIS C 1602: 1995 thermocouple (paragraph 44, reference 2 Fig. 1).
Japanese Industrial Standards JIS Z 3198-1: 2003, "lead free solder testing method-part 1: melting temperature range measuring method".

* cited by examiner

Primary Examiner—Lisa M Caputo
Assistant Examiner—Mirellys Jagan
(74) Attorney, Agent, or Firm—Brinks Hofer Gilson & Lione (57) ABSTRACT

It is discovered that a range of showing a state in which a sample is at a constant temperature at a freezing temperature by a latent heat can be specified from a result of a differential scanning calorimetry in a cooling procedure and a method of acquiring the freezing point of the sample from data in the range is shown. For example, an output temperature of an intersection constituted by a tangential line extrapolated from a DSC curve, an output temperature curve, and a base line or an extension of a range brought into a liquid state including a supercooled state is read, and a method of analyzing the DSC curve, the output temperature curve constituting the freezing point of the sample by a temperature of the intersection is discovered and adopted.

18 Claims, 8 Drawing Sheets

FREEZING POINT TEMPERATURE MEASURING METHOD AND TEMPERATURE CALIBRATING METHOD IN DIFFERENTIAL SCANNING CALORIMETRY

This application claims priority under 35 U.S.C. §119 to Japanese Patent Application No. JP2006-035265 filed Feb. 13, 2006, the entire content of which is hereby incorporated by reference.

BACKGROUND OF THE INVENTION

The present invention relates to a method of analyzing a DSC curve for accurately acquiring a freezing point of a sample showing supercooling by differential scanning calorimetry, and a method of carrying out temperature calibration in cooling of a differential scanning calorimetric apparatus by using a sample evaluated with a freezing point.

Figure 2:
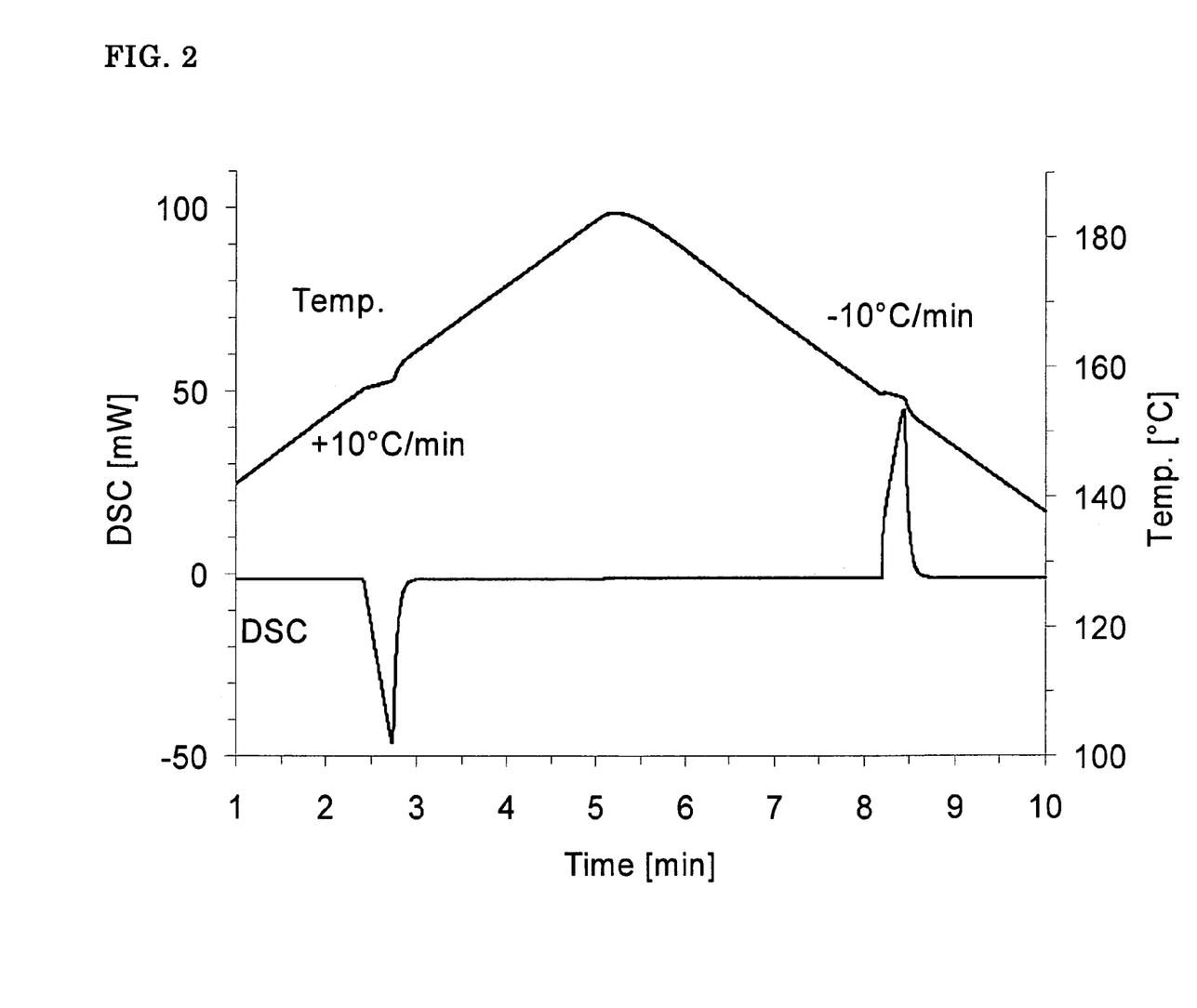
FIG. 2 shows a DSC curve of melting, freezing indium.

In differential scanning calorimetry of a background art, a freezing point of a sample showing supercooling is not acquired, or a crystallizing temperate is read as shown in FIG. 2 of Nonpatent reference 1 (see below) and Nonpatent Reference 2 (see below).

Nonpatent Reference 3 (see below) shows a method of measuring an evaluated freezing point of a sample by a crucible method as a temperature calibrating method of a thermocouple. A freezing point is measured by inserting a thermocouple directly into a sample, and therefore, when a temperature of the sample is made to be constant at a freezing point, a temperature curve shows a horizontal flat region, and therefore, it is known that the temperature may be read as it is.

Nonpatent Reference 4 (see below) shows an example of measuring a freezing point by a crucible method by directly inserting a thermocouple similarly into a sample of lead free solder. In order to firmly measure a flat region, an amount of the sample is an extraordinary large amount in comparison with that in differential scanning calorimetry.

[Nonpatent Reference 1] Japanese Industrial Standards JIS K 7121: 1987 transition temperature measuring method of plastic (paragraphs 4-5, FIG. 2, example of method of acquiring crystallizing temperature)

[Nonpatent Reference 2] ISO 11357-1: 1997 Plastics-Differential scanning calorimetry (DSC)-Part 1: General principles page 33. 10 characteristic temperatures, Page 5, 8. 2 Temperature calibration

[Nonpatent Reference 3] Japanese Industrial Standards JIS C 1602: 1995 thermocouple (paragraph 44, reference 2 FIG. 1)

[Nonpatent Reference 4] Japanese Industrial Standards JIS Z 3198-1: 2003 lead free solder testing method-part 1: melting temperature range measuring method According to the freezing point temperature measuring method in differential scanning calorimetry of a background art, as shown by FIG. 2 of above Nonpatent Reference 1, the crystallizing temperature is read, however, according to the method, with regard to a case of a sample showing supercooling, a temperature in correspondence with a temperature of staring to freeze a supercooled liquid is read, the temperature is a temperature which differs from the freezing point.

Further, although according to a method other than the differential scanning calorimetry, there is a method of measuring a temperature by directly inserting a thermocouple to a sample, in view of a structure of a differential scanning calorimetric apparatus, the thermocouple cannot directly be inserted into the sample and also an amount of the sample which can be installed in the apparatus is limited. Therefore, a systematic error by a heat flow is produced in a temperature measured value, and it is difficult to realize a stable freezing procedure over a long period of time since the sample amount is small.

It is a problem of the invention to provide a method of analyzing a DSC curve, an output temperature curve for acquiring an accurate freezing point from a result of differential scanning calorimetry and a temperature calibrating method in cooling a differential scanning calorimetric apparatus even in a sample showing supercooling.

SUMMARY OF THE INVENTION

In order to resolve the above-described problem, according to a freezing point measuring method based on an analysis of a DSC curve or an output temperature range of the invention.

First, the method is characterized in acquiring a freezing point of a sample by lowering a temperature of a sample showing supercooling to cool to be subjected to a differential scanning calorimetry, specifying a time range or an output temperature range showing a state in which the sample is at a constant temperature at a freezing temperature in a DSC curve or an output temperature curve provided by the calorimetry, and using the DSC curve or the output temperature curve in the specified temperature range or the specified output temperature range.

Second, the method is characterized in that in the DSC curve, in a measurement of cooling in which the temperature of the sample is lowered at a constant rate, in a heat generating peak portion of a procedure of freezing the sample from a supercooled liquid, an output temperature of an intersection of an extrapolated tangential line of a portion brought into the time range or the output temperature range showing the state in which the sample is at the constant temperature at the freezing point and a base line of a range constituting a liquid state including a supercooled state or an extrapolated tangential line of the base line is read and the freezing point of the sample is constituted by the temperature of the intersection.

Third, the method is characterized in that in the output temperature curve, in a measurement of cooling in which the temperature of the sample is lowered at a constant rate, in a heat generating region of a procedure of freezing the sample from a supercooled liquid, an output temperature of an intersection of an extrapolated tangential line of the time range showing the state in which the sample is at the constant temperature at the freezing temperature and an output temperature linear line in a range constituting a liquid state including a supercooled state or an extrapolated tangential line of the output temperature linear line is read and the freezing point of the sample is constituted by the temperature of the intersection.

Fourth, the method is characterized in that in the DSC curve, in a heat generating peak portion of a procedure of freezing the sample from a supercooled liquid, in a portion of the time range or the output temperature range showing the state in which the sample is at the constant temperature at the freezing temperature, a first data set formed by a temperature and a DSC value at a certain point, and a second data set formed by a temperature and a DSC value at a different time point are formed, and the freezing point of the sample is acquired by calculating a correlative relationship between the data sets.

Fifth, the method is characterized in that in the DSC curve and the output temperature curve, in a heat generating peak portion of a procedure of freezing the sample from a supercooled liquid, in a portion disposed in the time range or the output temperature range showing the state in which the sample is at the constant temperature at the freezing temperature, a temperature and a DSC value at a certain time point are acquired, a thermal resistance value between the sample and an output temperature measuring point is provided previously, and the freezing point of the sample is acquired by adding a product provided by multiplying the DSC value by the thermal resistance value to the temperature at the certain time point.

Sixth, a temperature calibrating method is characterized in calibrating an output temperature of a thermocouple of a differential scanning calorimetric apparatus, wherein with regard to a sample evaluated with a freezing point, a freezing point of the sample is acquired by using the freezing point measuring method according to the above-described first method, a temperature difference between the acquired freezing point and the evaluated freezing point of the sample is calculated, a corrected value is calculated from the temperature difference; and the evaluated freezing point is shown. Further, the above-described first freezing point measuring method is a freezing point measuring method, wherein a temperature of a sample showing supercooling is lowered to be cooled to be subjected to a differential scanning calorimetry, in a DSC curve or an output temperature curve provided by the calorimetry, a time range or an output temperature range showing a state in which the sample is at a constant temperature at a freezing temperature is specified, and a freezing point of the sample is acquired by using the DSC curve or the output temperature curve in the specified time range or the specified output temperature range.

Figure 4:
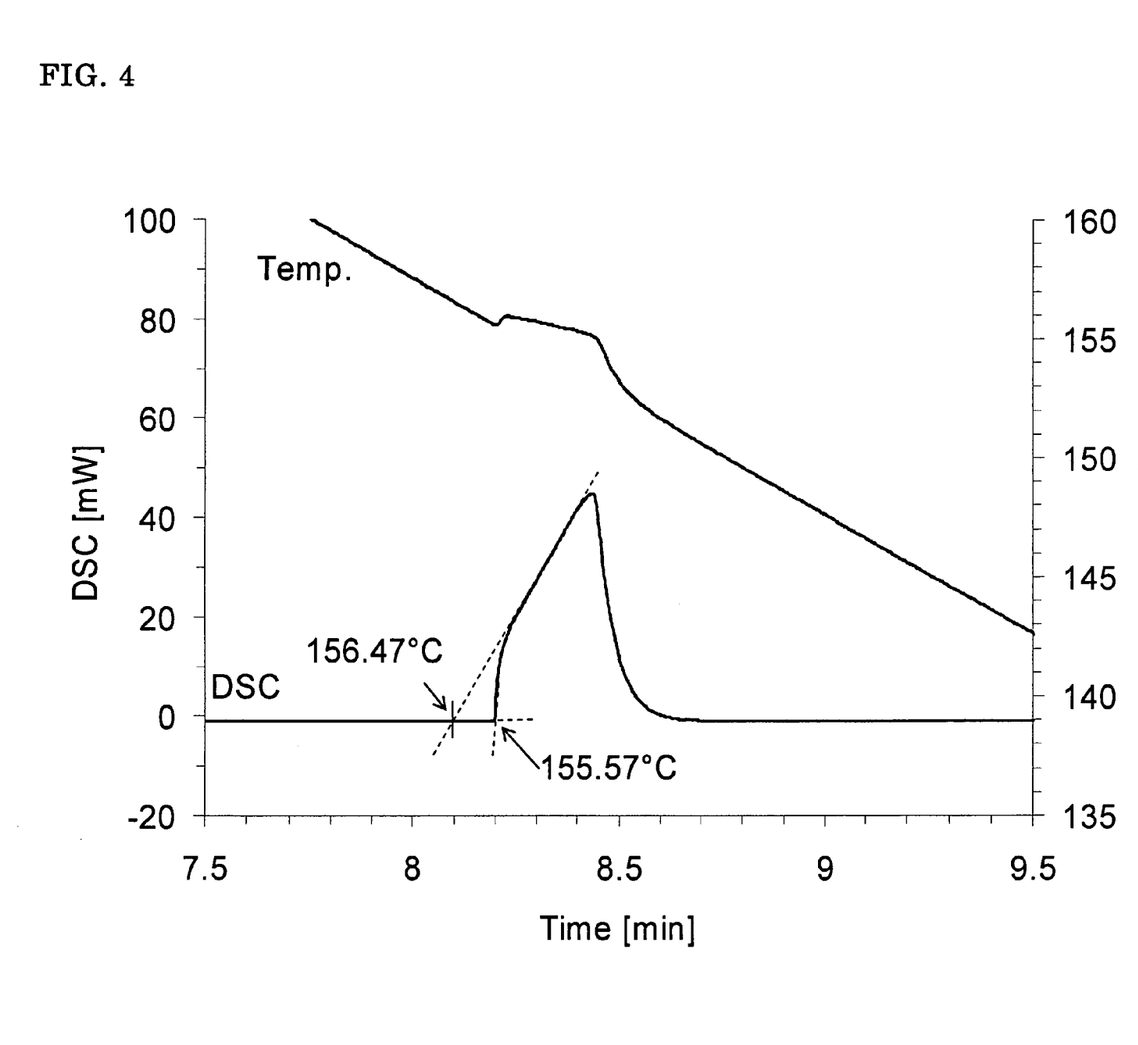
FIG. 4 shows a DSC curve (1) of freezing indium.

A method of analyzing the DSC curve of the invention is based on a discovery that as shown by a DSC curve (1) of freezing indium of FIG. 4, in a heat generating peak in freezing a sample, with regard to a region showing a constant rightward rising inclination, there is provided a range showing a state in which the sample is at the constant temperature at the freezing temperature. By using data of the range, even in a sample showing supercooling, the freezing point can accurately be calculated. For example, there is discovered and adopted a method of analyzing the DSC curve, the output temperature curve, in which an output temperature of an intersection of an extrapolated tangential line from the DSC curve, the output temperature curve, and a base line of a range constituting a liquid state including a supercooled state or an extension thereof is read and the freezing point of the sample is constituted by the temperature of the intersection.

Further, in a case a sample having an evaluated freezing point as in, for example, indium, when a temperature difference between the evaluated freezing point and a freezing point acquired by an actual measurement is calculated, it is known to what degree the output temperature measured by the thermocouple or the like of the differential scanning calorimetric apparatus is shifted, and therefore, the temperature calibration of the apparatus can be carried out by constituting a temperature corrected value by the temperature difference.

The invention achieves an effect described below.

According to the method of analyzing the DSC curve constituted as described above, the freezing point of the sample showing supercooling which has not been accurately calculated in the background art, can accurately be calculated. Further, since the freezing procedure is brought about in measurement of cooling, the temperature calibration of the differential scanning calorimetric apparatus in the measurement of cooling in which the temperature is lowered at the constant rate which cannot be carried out in the background art, can be carried out.

DETAILED DESCRIPTION OF THE PREFERRED EMBODIMENTS

An embodiment of the invention will be explained in reference to the drawings.

Figure 1:
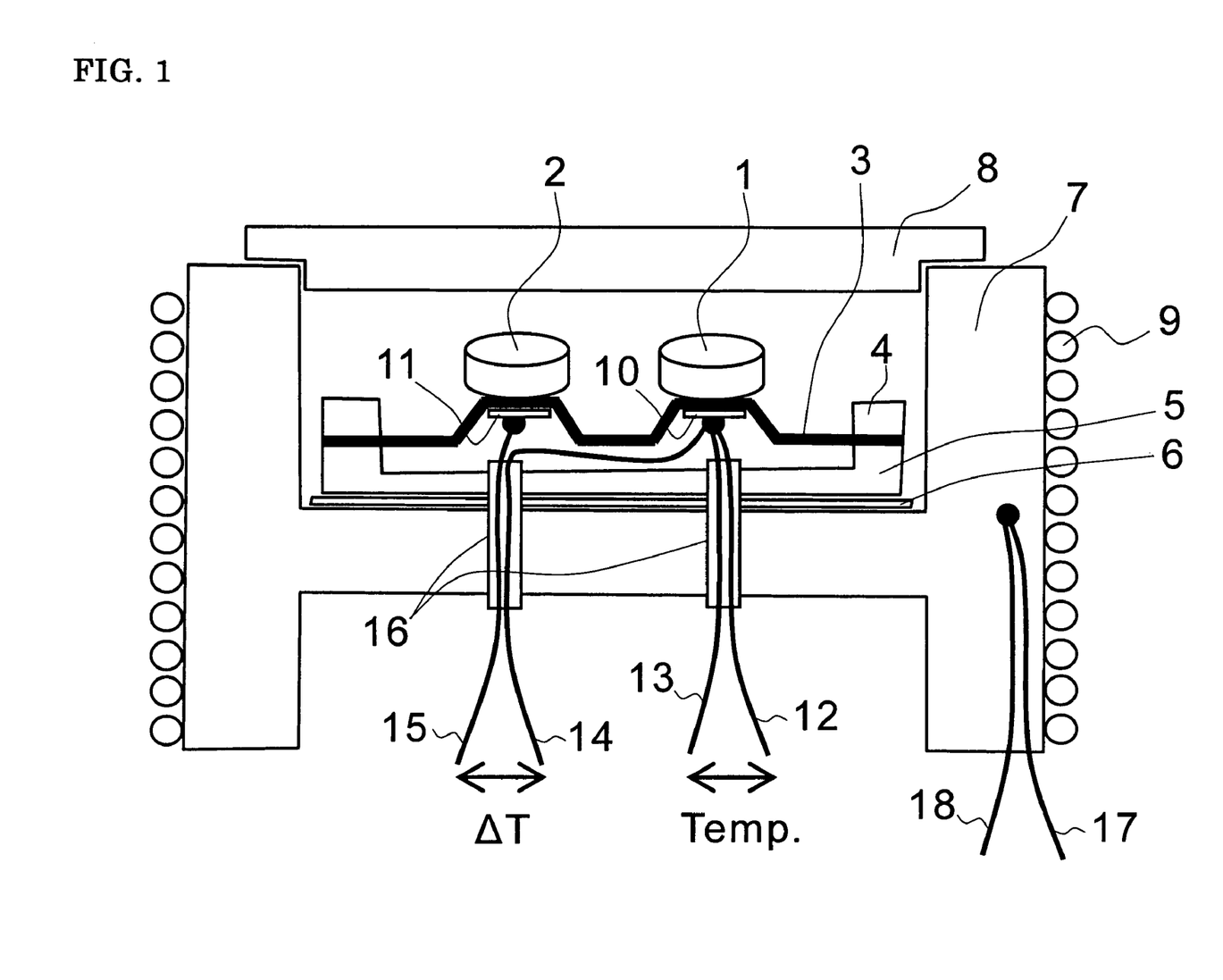
FIG. 1 is a sectional view of a sensor portion of an example of a differential scanning calorimetric apparatus.

FIG. 1 shows an example of a differential scanning calorimetric apparatus used in the invention, and a sectional view of a sensor portion. The apparatus of FIG. 1 is an example disclosed in Japanese Patent No. 3137605 (See FIG. 1). The apparatus is a representative example and the invention is generally applicable to a differential scanning calorimetric apparatus in which a temperature sensor is not directly inserted into a sample.

A sample vessel 1 and a reference substance vessel 2 are made of aluminum, a size thereof is about 5 mm in a diameter, a sample showing supercooling is put into the sample vessel 1, a reference substance of aluminum or alumina powder or the like is put into the reference substance vessel 2, normally, a lid made of aluminum is covered thereon to be crimped. Amounts of the sample and the reference substance are normally several mg through several 10 mg. The respective vessels are placed at predetermined positions of a heat conductive plate 3 made of constantan designed such that a thermal resistance thereof becomes a value as aimed. The constantan heat conductive plate 3 is in a shape of a circular plate in a case of this example, pinched by a silver upper side holding plate 4 and a silver lower side holding plate 5 and is held to maintain excellent thermal contact with the respective holding plates. The silver lower side holding plate 5 is fixed to a silver heat sink 7 by interposing a heat buffer plate 6 therebetween. The silver heat sink 7 is a cylinder having a section in an H shape, provided with a size of about 40 mm in diameter and 30 mm in height and envelopes the respective sample vessels and the constantan made heat conductive plate 3. A silver lid 8 is covered thereon, prevents heat from being transferred to an outer field by radiation from the sample vessel 1, the reference substance vessel 2, the constantan heat conductive plate 3 or convection of air, and prevents noise by a nonuniformity in a temperature produced by making air flow in from the outer field. A surrounding of the silver heat sink 7 is wound with a heater 9 for heating, the silver heat sink 7 is cooled from surrounding by a cooler, not illustrated, a temperature thereof is changed by a desired rate to construct a constitution capable of elevating temperatures, cooling temperatures, maintaining equal temperatures by a constant rate or various patterns.

A back side of the constantan heat conductive plate 3 is respectively welded with a sample side chromel plate 10 and a reference side chromel plate 11 to constitute contacts of a thermocouple constituted by chromel and constantan. The respective chromel plates are welded with a chromel wire and an alumel wire as shown by the drawing to constitute the thermocouple, and an electromotive force signal of a sample temperature provided by a chromel wire 12 and an alumel wire 13 covered with an insulating tube 16 and an electromotive force signal of a temperature difference ΔT between the sample and the reference substance by chromel wires 14, 15 covered with an insulating tube 16 are measured by a detector, not illustrated. In measuring the sample temperature and the temperature difference ΔT, these are measured at a middle of a path of a heat flow flowing in from the silver heat sink 7 to the respective vessels or flowing out from the respective vessels to the silver heat sink 7.

Further, the silver heat sink 7 is fixed with one set of thermocouple by a chromel wire 17 and an alumel wire 18 to be measured by a detector, not illustrated, and a temperature of the silver heat sink 7 is controlled to elevate a temperature, cool, maintain at an equal temperature at a constant rate or various patterns by the heater 9 and a cooler, not illustrated, which are controlled by a power controller, not illustrated.

In order to accurately detect the heat flow, as shown by FIG. 1, a point of detecting the temperature difference ΔT signal needs to be provided outside of the sample, which constitutes a characteristic of the differential scanning calorimetric apparatus. Therefore, the temperature of the sample is not directly measured but a temperature of a position interposing the vessel, the heat conductive plate and the like therebetween is measured, which constitutes a factor of making freezing point measurement difficult. According to the differential scanning calorimetric apparatus at this time, a sensor shortening a heat flow response time is fabricated and is used for the measurement, and therefore, a procedure of freezing while elevating a temperature at and below a freezing temperature and a procedure of freezing at a freezing temperature while making a temperature constant which has been unable to be discriminated in a background art, can clearly be separated. Thereby, two kinds of freezing start temperatures, that is, an extrapolated freezing start temperature and an extrapolated freezing start temperature of a supercooled liquid can respectively calculated by drawing an ancillary line to the DSC curve or the output temperature curve, or analytically from the DSC value and the output temperature value. The freezing point is the extrapolated freezing start temperature in the two kinds of freezing start temperatures.

FIG. 2 shows graphs of a DSC curve, a temperature curve when indium of 20.07 mg is packed into the aluminum vessel and covered with the similarly aluminum lid to be crimped and the curves are measured at a temperature elevating rate of +10° C. per minute, a temperature lowering rate of −10° C. per minute by the apparatus of FIG. 1. A heat absorbing peak by melting and a heat generating peak by freezing are observed at a vicinity of 156° C. Indium is a metal that is evaluated with a freezing point, is provided with a freezing point at a temperature region in which measurement is carried out most frequently, is characterized in being soft and easy to be sampled, easy to be obtained, stored, and is used in temperature calibration of a differential scanning calorimetric apparatus most generally.

Figure 3:
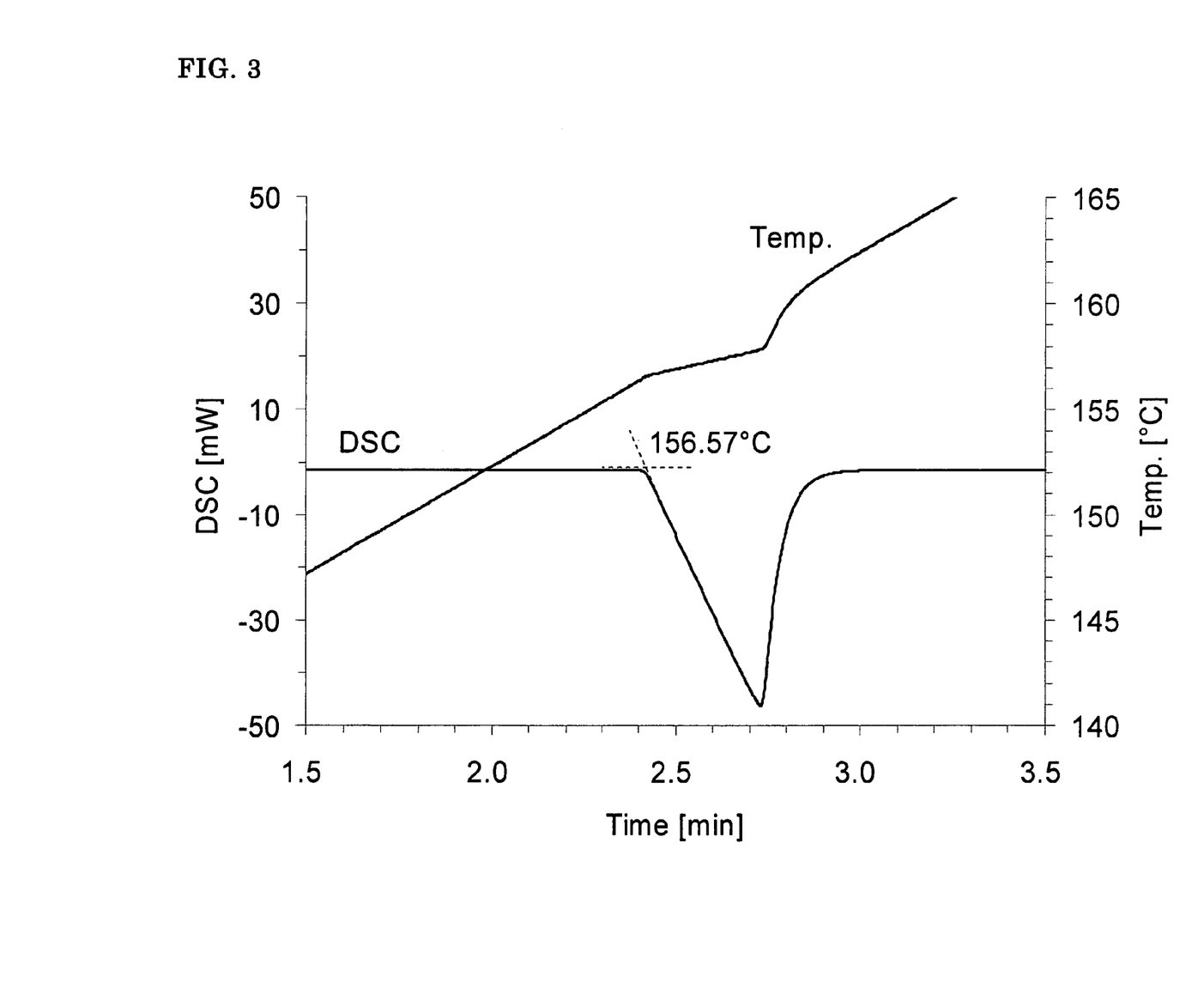
FIG. 3 shows a DSC curve of melting indium.

FIG. 3 is a graph enlarging a melting peak portion of FIG. 2. When a temperature of a freezing point is read by the melting peak, as shown by the drawing, there is acquired an output temperature of an intersection constituted by a base line or an extension in a solid state before being frozen, and a tangential line drawn from a region in which the temperature of the sample is made to be constant and the DSC curve shows a constant inclination in a melting procedure. In a case of FIG. 3, the output temperature has been 156.57° C. A state in which the temperature of the sample is constant in the melting procedure is a state in which the temperature is constant at the freezing point and a liquid and a solid are coexistent. In operating to acquire the intersection as described above, the output temperature when the temperature is constant at the freezing point and a heat flow by latent heat is null.

According to the method, the method is not influenced by the latent heat of the sample, the output temperature is the most proximate to the transition temperature, and the output temperature can be read with excellent reproducibility.

Further, the output temperature includes two kinds of errors. One is an error of the thermocouple and a detecting system, other is a temperature difference generated in accordance with Newton's law of cooling by a heat flow flowing to the vessel and the sample and a thermal resistance between sample-thermocouple contacts. When a sample of indium or the like evaluated with the freezing point is measured as shown by FIG. 3, a magnitude of an error under a certain condition of a temperature elevating rate is known, and therefore, when correction is carried out such that the magnitude is nullified, the temperature calibration can be carried out under the certain condition of the temperature elevating rate.

The latter error in the two kinds of errors establishes a relationship represented by a linear equation of the temperature elevating/lowering rate as follows. When the temperature elevating rate is defined to be plus and the temperature lowering rate is defined to be minus, the magnitude of the heat flow flowing into the vessel and the sample is constituted by a value of a heat capacity multiplied by the temperature elevating/lowering rate and therefore, proportional to the temperature elevating/lowering rate, further, the temperature difference produced in accordance with Newton's law of cooling becomes a value of the heat flow flowing to the vessel and the sample multiplied by the thermal resistance between the sample-thermocouple contacts, and therefore, proportional to the temperature elevating/lowering rate. The latter error establishes the relationship represented by the linear equation of the temperature elevating/lowering rate.

FIG. 4 is a graph enlarging the freezing peak portion of FIG. 2. When freezing is started, it is observed that the temperature of the sample is temporarily elevated, thereby, it is known that a supercooled state is brought about. When the temperature of the freezing point is read by the freeing peak, as shown by the drawing, there is acquired an output temperature of an intersection constituted by a base line or an extension thereof of a liquid before being frozen or the liquid in the supercooled state, and a tangential line drawn from a region in which the temperature of the sample is constant in the freezing procedure and the DSC curve shows a constant inclination. In the case of FIG. 4, the output temperature has been 156.47° C. A state in which the temperature sample is constant in the freezing procedure is a state in which the temperature is constant at the freezing point and the liquid and the solid are coexistent. Operation of acquiring the intersection as described above is operation of acquiring an extrapolated freezing start temperature, and an output temperature when the temperature is constant at the freezing point and the heat flow by the latent heat is nullified is read.

According to the method, the method is not influenced by the latent heat of the sample, the output temperature is the most proximate to the transition temperature, and the output temperature can be read with an excellent reproducibility.

Here, when there are conceived peaks shape in which portions of starting the peaks are brought into a supercooled state in the DSC curve and the output temperature curve which are respectively made to be upside down at the melting peak of FIG. 3, the peak shapes become the shapes of the graph of FIG. 4 and therefore, it is easy to understand that the temperature read as 156.47° C. becomes the freezing point.

In FIG. 4, there is another point of the temperature read as 155.57° C. This is the temperature constituted by reading an intersection constituted by the base line or the extension of the supercooled state of the liquid and a tangential line drawn from the region of the procedure of freezing the sample while the temperature of the sample is being elevated at or below the freezing temperature. The temperature corresponds to the extrapolated freezing start temperature of the supercooled liquid. When the tangential line is drawn from a point having a maximum inclination in a total of the freezing peak, the point is read.

Figure 5:
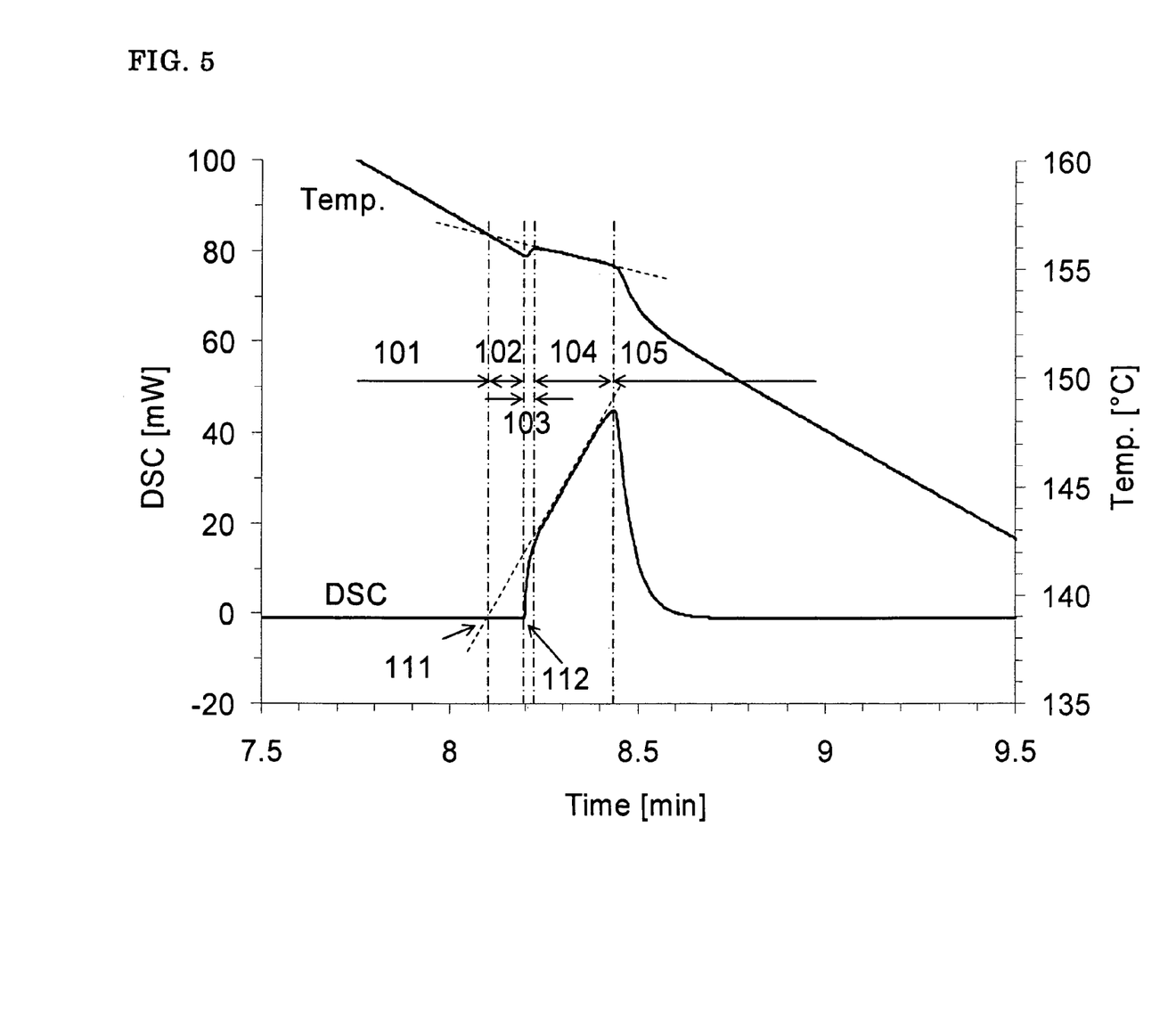
FIG. 5 shows a DSC curve (2) of freezing indium.

FIG. 5 is a diagram for explaining drawing vertical one-dotted broken lines and partitioning the state of the sample at every time region in FIG. 4. At region 101, the temperature is higher than the freezing point 111 constituting the extrapolated freezing start temperature and the sample is brought into a liquid state. At region 102, the temperature is lower than the freezing point 111 and the sample is brought into the supercooled state of the liquid. Region 103 shows a procedure of freezing the supercooled liquid while elevating the temperature by discharging the latent heat at and below the freezing point. The region is a small region having a time period of 2 seconds or less. A boundary between the regions 102 and 103 is a read point 112, corresponds to the extrapolated freezing start temperature of the supercooled liquid and is 155.57° C. as described above. Region 104 is a region in which the sample discharges the latent heat in the freezing procedure, the temperature of the sample is constant, the liquid and the solid are coexistent and the DSC curve shows a constant inclination. Region 105 shows a transition procedure in which the freezing procedure is finished, all of the sample becomes solid, and the temperature is lowered at a constant rate from the state of the constant temperature of the freezing point.

Further, also in the output temperature curve, it is known that an intersection constituted by the output temperature curve of the liquid before being frozen or the supercooled state of the liquid or an extension thereof, and a tangential line drawn from a region in which the temperature of the sample is constant in the freezing procedure and the output temperature curve shows a constant inclination constitutes a boundary of the regions 101 and 102, and it is known that the freezing point can be acquired similarly by the output temperature curve.

Both in the DSC curve and in the output temperature curve, when a degree of supercooling is much smaller than that of supercooling of FIG. 4, the region is to be shifted to the region 104 while the width of the region 103 is narrow and the height from the base line is low. In that case, the intersection cannot be acquired on the base line of the DSC curve of the liquid before being frozen or the liquid in the supercooled state or on the output temperature curve and therefore, the freezing point can be read by drawing an extension and constituting the intersection on the extension. The base line of the DSC curve or the output temperature curve of the liquid before being frozen or the liquid in the supercooled state is constituted by a shape of a long linear line when the temperature of the sample is lowered at a constant rate and therefore, the extension and the extrapolated tangential line become the same.

Figure 6:
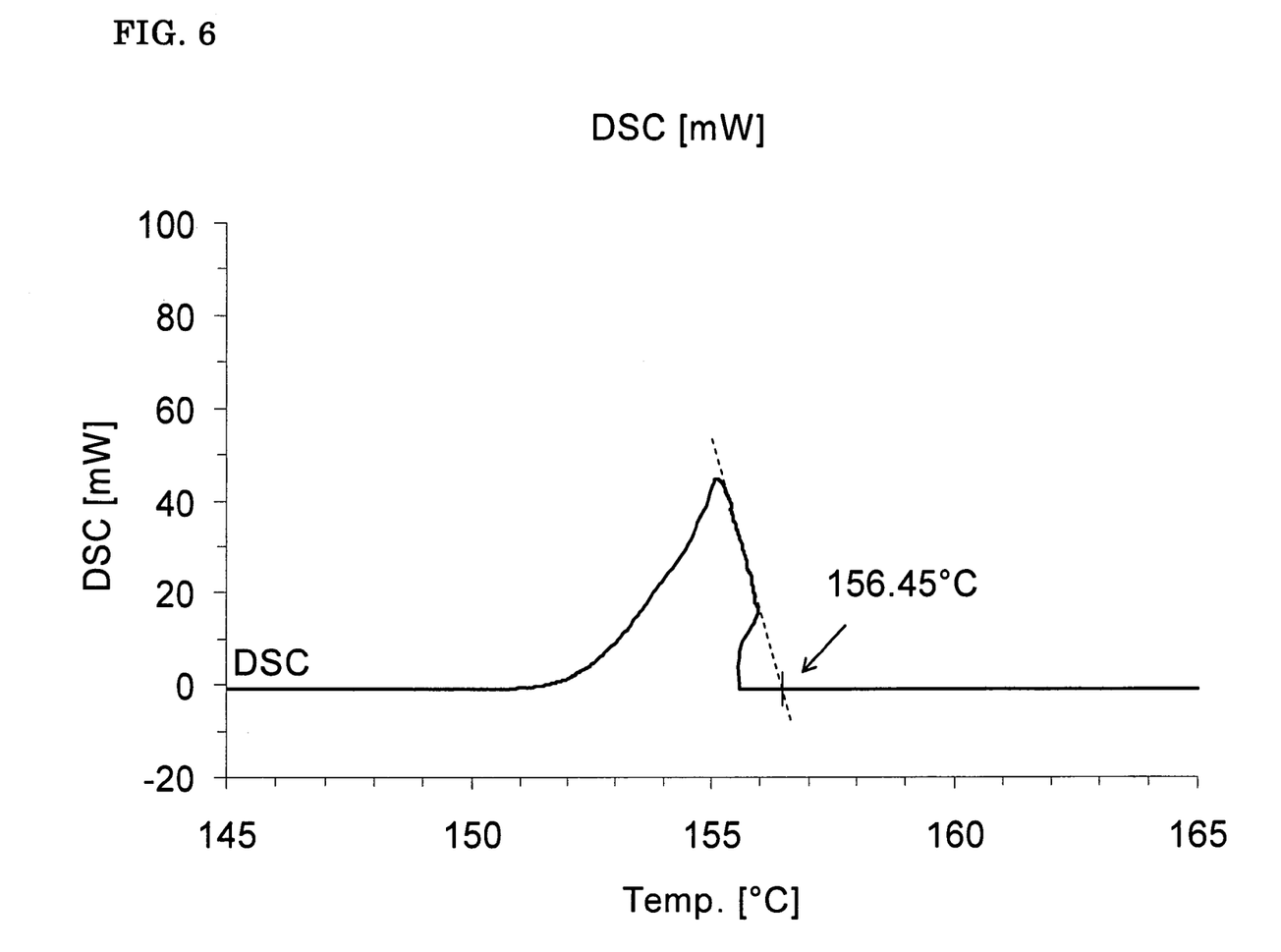
FIG. 6 shows a DSC curve (3) of freezing indium.

FIG. 6 shows data redisplaying data of FIG. 4 by constituting a temperature axis by the abscissa. Also in this case, similar to FIG. 4, there is acquired an output temperature of an intersection constituted by the base line of the liquid before being frozen or the liquid in the supercooled state or the extension, and the tangential line drawn from the region in which the temperature of the sample is constant in the freezing procedure and the DSC curve shows a constant inclination. In the case of FIG. 6, the output temperature is 156.45° C., which is substantially the same as the extrapolated freezing start temperature read in FIG. 4.

Methods shown in FIGS. 4, 5, 6 are methods of using data measured by the constant temperature lowering rate in cooling and are generally-used methods acquired by drawing diagrams.

Figure 7:
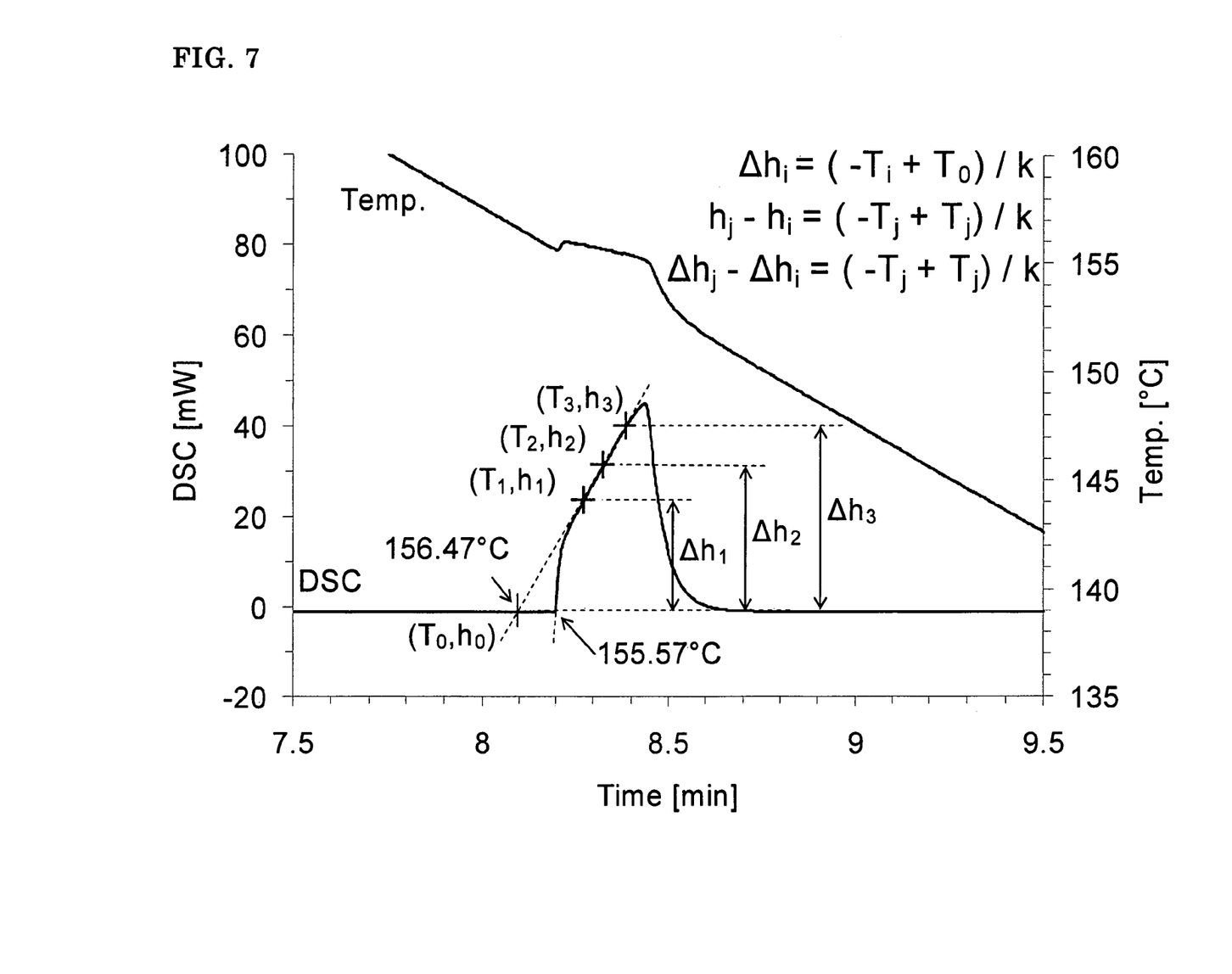
FIG. 7 shows a DSC curve (4) of freezing indium.

FIG. 7 is a diagram showing sets of data of output temperatures Ti and DSC values hi on the DSC curve of FIG. 4. Notations i and j indicate 1, 2, 3, notations (Ti, hi) and (Tj, hj) indicate arbitrary points of a region in which the temperature of the sample is constant in the freezing procedure. Notation T0 indicates the freezing point, notation h0 indicates the DSC value when the temperature is T0. Notation $\Delta hi$ indicates a height from the base line before and after the peak. The data take values in accordance with 3 pieces of calculating equations shown in the drawing. Notation k designates the thermal resistance value between points of measuring temperatures of sample-sample. When k is unknown, at least 2 pieces or more of data sets are needed. When the freezing point T0 is actually calculated from 3 pieces of (Ti, hi) by the least squares method, the freezing point T0 becomes 156.47° C., which coincides with a numerical value acquired in FIG. 4. In this way, the freezing point can also be calculated from a correlative relationship among the sets of data. Since k can separately be calculated by analyzing the melting peak, the freezing point T0 can also be calculated not by a plurality of data sets but by a single thereof.

It can be devised to previously input a pertinent value of k and correcting and recording the output temperature while calculating a temperature value to be corrected from the DSC value by a calculation. A method of correcting the temperature difference generated in accordance with Newton's law of cooling by the heat flow flowing to the vessel and the sample and the thermal resistance between the contacts of the sample-thermocouple is a method of correcting the temperature difference by adding a value of the DSC value or the hi value multiplied by the thermal resistance value k to the output temperature. When the hi value is used, the hi value can be calculated by previously measuring DSC of the reference substance in place of a substance to be frozen and recording a base line of the reference substance and subtracting the base line from the DSC curve of the freezing peak. According to the method, even when the drawing is not drawn later, at a region in which the temperature of the sample is constant in the melting and freezing procedure, also the output temperature is already constant horizontally. The region is easy to specify and when one point is read in the region, the freezing point can simply be calculated.

Further, according to the analytical method shown in FIG. 7, the method achieves an advantage of being able to be applied even when the temperature lowering rate in cooling is not constant and the temperature lowering rate is changed in the freezing procedure. When in accordance with lowering the temperature, also the temperature lowering rate is gradually reduced as in natural cooling in which a cooler is not used, when freezing is started from a supercooled state of a liquid, a region of a procedure of being frozen while elevating the temperature of the sample at and below the freezing temperature appears in the DSC curve, successively, a region in which the temperature of the sample is constant in the freezing procedure and the DSC curve shows a constant inclination appears. In this case, when the temperature lowering rate is gradually reduced, an amount of generating heat of the sample becomes smaller than that when the temperature lowering rate is constant and a height of a heat generating freezing peak is reduced. The DSC curve is constituted by a shape in which the inclination is not constant but the inclination is gradually reduced. Since a total heat generating amount of freezing remains unchanged, a time period of the region of the constant temperature of the sample is prolonged and the height is lowered and a peak area of the graph remains unchanged. In a case in which when the temperature lowering rate is changed, also the base line is changed, the same temperature change may be previously applied to a reference substance in place of a substance to be frozen and a base line may be recorded and the base line may be subtracted from the DSC curve. In this way, even when the temperature lowering rate is not constant but is changed and the shape of the freezing peak is changed, according to the analytical method shown in FIG. 7, the respectives of (Ti, hi) follow the same calculating equation and therefore, the freezing point can accurately be calculated.

Naturally, even when the temperature lowering rate is gradually increased conversely, or periodically changed, the respectives of (Ti, hi) similarly follow the same calculating equation and the freezing point can accurately be calculated.

Figure 8:
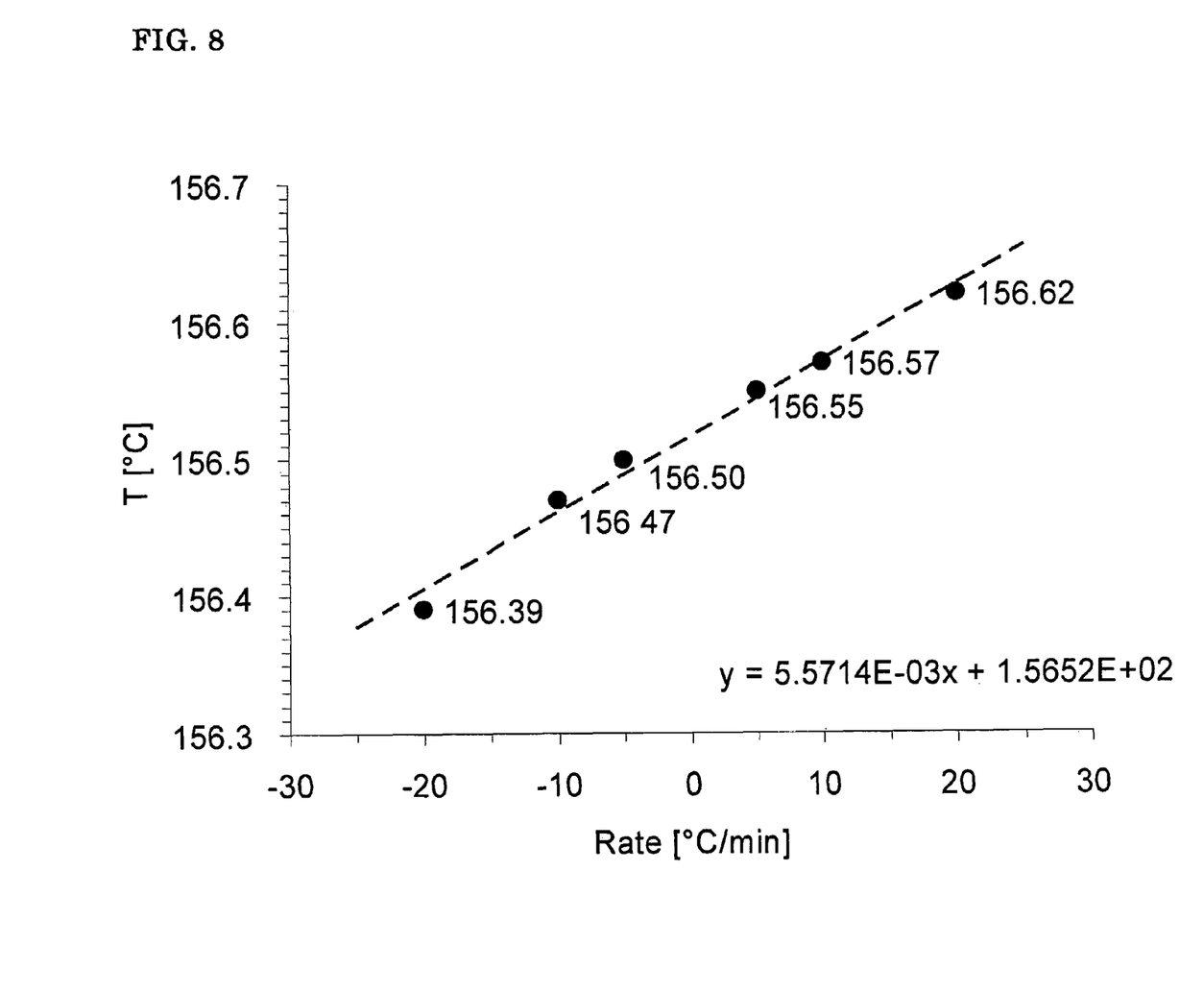
FIG. 8 shows a relationship between a result of measuring a freezing point of indium and a temperature elevating/lowering rate.

FIG. 8 displays a result T [° C.] of reading respective extrapolated freezing start temperatures when the temperature elevating/lowering rate is +20, +10, +5, −5, −10, −20 (+indicates elevating temperature, −indicates lowering temperature) [° C./min] on a graph. It is known that the extrapolated freezing start temperature is brought into substantially a linear relationship with the temperature elevating/lowering rate. By the least squares method, the inclination can be calculated as 0.00557° C. per 1° C./min and the segment can be calculated as 156.52° C.

When the evaluated freezing point of indium is 156.60° C., the magnitudes of two kinds of errors of the output temperature can be estimated. Since the former is the error of the thermocouple and the detecting system, the error is a temperature when the latter error is nullified by interpolating the temperature elevating/lowering rate to null, that is, a difference between the segment and the evaluated freezing point and therefore, the error can be estimated as 156.52−156.60=−0.08° C. Further, since the latter is the temperature difference produced by the heat flow flowing into the vessel on the sample and the thermal resistance between the sample-thermocouple contacts, the heat flow is proportional to the temperature elevating/lowering rate, also the produced temperature difference is proportional to the temperature elevating/lowering rate, and therefore, the error becomes the previously calculated inclination and can be estimated as 0.00557° C. per 1° C./min. From the result, the temperature calibration at the respective temperature elevating/lowering rates can be carried out.

As described above, an explanation has been given referring to an example of a result of measuring indium, it is shown that the method of calculating the freezing point by the heat generating peak of the procedure of freezing from the supercooled liquid can be carried out, further, it is known that when the sample having the evaluated freezing point is measured, the temperature can be calibrated from the result.

Other than indium, in lead, a freezing point can similarly be calculated. The freezing point of lead is 327.6° C., and therefore, a temperature calibration by two points can be carried out by indium and lead. According to tin having a freezing point of 232.0° C., a magnitude of supercooling is as large as about 50° C., and therefore, freezing is completely finished in the midst of the region 103, and therefore, the region 104 does not appear and the freezing point cannot be acquired. However, when there is a method of reducing the magnitude of supercooling, the method of the invention is applicable thereto. Also in another sample showing supercooling, the freezing point can be acquired by applying the method of the invention.

In this way, it seems that measurement of the freezing point by differential scanning calorimetry has not been discovered and has not been embodied in the background art because the thermocouple cannot directly be inserted into the sample, and therefore, the measurement error by a heat flow is brought about, further, since the amount of the sample is small, it has been conceived to be difficult to realize a stable freezing procedure for measurement.

What is claimed is:

1. A freezing point measuring method of acquiring a freezing point of a sample, comprising:

lowering a temperature of a sample showing supercooling to cool to be subjected to a differential scanning calorimetry;

specifying a time range or an output temperature range showing a state in which the sample is at a constant temperature at a freezing temperature in a DSC curve or an output temperature curve provided by the calorimetry; and using the DSC curve or the output temperature curve in the specified temperature range or the specified output temperature range to acquire the freezing point of the sample, wherein in the DSC curve and the output temperature curve, in a heat generating peak portion of a procedure of freezing the sample from a supercooled liquid, in a portion disposed in the time range or the output temperature range showing the state in which the sample is at the constant temperature at the freezing temperature, a temperature and a DSC value at a certain time point are acquired, a thermal resistance value between the sample and an output temperature measuring point is provided previously, and the freezing point of the sample is acquired by adding a product provided by multiplying the DSC value by the thermal resistance value to the temperature at the certain time point.

2. A temperature calibrating method of calibrating an output temperature of a thermocouple of a differential scanning calorimetric apparatus, comprising:

acquiring a freezing point of the sample whose freezing point is known, using the freezing point measuring method according to claim 1;

calculating a temperature difference between the acquired freezing point and the known freezing point of the sample;

calculating a corrected value from the temperature difference; and calibrating an output temperature of the thermocouple to the known freezing point.

3. A method of measuring a freezing temperature of a sample exhibiting a supercool state, using a DSC, the method comprising:

cooling the sample and a reference material to observe solidification of the sample in a liquid state;

monitoring, while cooling the sample and the reference material, temperature differential values between the sample and the reference material and temperature values of the sample obtained at the DSC over a period of time including a solidifying time period which begins with an initiation of solidification of the sample in the liquid state and ends with a completion of solidification thereof;

identifying a range of the temperature differential values which defines a state of the sample in which latent heat from the sample substantially offsets cooling of the sample; and determining the freezing temperature from a temperature value of the sample corresponding to an intersection between an imaginary line tangential to at least a part of the temperature differential values monitored within the range and an imaginary line tangential to at least a part of the temperature differential values monitored outside the solidifying time period.

4. A method of determining a calibration value of outputs from a DSC, comprising:

determining the freezing temperature of a sample using the method according to claim 3, and obtaining the calibration value from a difference between the determined freezing temperature and a known freezing temperature of the sample.

5. A method according to claim 3, wherein cooling the sample and a reference material comprises cooling the sample and a reference material at a constant rate.

6. A method of measuring a freezing temperature of a sample exhibiting a supercool state, using a DSC, the method comprising:

cooling the sample to solidify the sample in a liquid state;

monitoring, while cooling the sample, temperature values of the sample obtained at the DSC over a period of time including a solidifying time period which begins with an initiation of solidification of the sample in the liquid state and ends with a completion of solidification thereof;

identifying a range of the temperature values which defines a state of the sample in which latent heat from the sample substantially offsets cooling of the sample; and determining the freezing temperature from a temperature value of the sample corresponding to an intersection between an imaginary line tangential to at least a part of the temperature values monitored within the range and an imaginary line tangential to at least a part of the temperature values monitored prior to the solidifying time period.

7. A method of determining a calibration value of outputs from a DSC, comprising:

determining the freezing temperature of a sample, using the method according to claim 6, and obtaining the calibration value from a difference between the determined freezing temperature and a known freezing temperature of the sample.

8. A method according to claim 6, wherein cooling the sample comprises cooling the sample at a constant rate.

9. A method of measuring a freezing temperature of a sample exhibiting a supercool state, using a DSC, the method comprising:

cooling the sample and a reference material to observe solidification of the sample in a liquid state;

monitoring, while cooling the sample and the reference material, temperature differential values between the sample and the reference material and temperature values of the sample obtained at the DSC over a period of time including a solidifying time period which begins with an initiation of solidification of the sample in the liquid state and ends with a completion of solidification thereof;

identifying a range of the temperature differential values which defines a state of the sample in which latent heat from the sample substantially offsets cooling of the sample;

using at least one temperature differential value and a corresponding temperature value within the range to derive a function of the temperature differential values and the temperature values within the range, wherein the function includes a thermal resistance between the sample and a temperature measuring point at the DSC for the sample; and determining the freezing temperature from a temperature value of the sample corresponding to an intersection between a line representative of the function and an imaginary line tangential to at least a part of the temperature differential values monitored outside the solidifying time period.

10. A method according to claim 9, wherein the thermal resistance is known.

11. A method according to claim 9, wherein the temperature differential values used in the function are indicative of heights from the imaginary line tangential to at least a part of the temperature differential values monitored outside the solidifying time.

12. A method according to claim 9, wherein cooling the sample and a reference material comprises cooling the sample and a reference material at a constant rate.

13. A method of determining a calibration value of outputs from a DSC, comprising:

determining the freezing temperature of a sample using the method according to claim 9, and obtaining the calibration value from a difference between the determined freezing temperature and a known freezing temperature of the sample 14. A method according to claim 9, wherein the thermal resistance is unknown.

15. A method according to claim 14, wherein using at least one temperature differential value and a corresponding temperature value within the range to derive a function of the temperature differential values and the temperature values within the range comprises using at least two temperature differential values and corresponding temperature values within the range to derive a function of the temperature differential values and the temperature values within the range, employing a least square method.

16. A method of measuring a freezing temperature of a sample exhibiting a supercool state, using a DSC, the method comprising:

cooling the sample and a reference material to observe solidification of the sample in a liquid state monitoring, while cooling the sample and the reference material, temperature differential values between the sample and the reference material and temperature values of the sample obtained at the DSC over a period of time including a solidifying time period which begins with an initiation of solidification of the sample in the liquid state and ends with a completion of solidification thereof;

modifying the temperature values by adding thereto corresponding temperature differential values multiplied by a known thermal resistance between the sample and a temperature measuring point at the DSC for the sample;

identifying a range of the modified temperature values which takes a constant temperature value; and determining the freezing point from the constant temperature value.

17. A method of determining a calibration value of outputs from a DSC, comprising:
  determining the freezing temperature of a sample using the method according to claim 16, and
  obtaining the calibration value from a difference between the determined freezing temperature and a known freezing temperature of the sample.

18. A method according to claim 16, wherein cooling the sample and a reference material comprises cooling the sample and a reference material at a constant rate.

* * * * *